US00PP33287P2

(12) United States Plant Patent
Farrow

(10) Patent No.: US PP33,287 P2
(45) Date of Patent: Jul. 27, 2021

(54) ***JUNIPERUS* PLANT NAMED 'FARROWJVBF'**

(50) Latin Name: *Juniperus virginiana*
Varietal Denomination: FARROWJVBF

(71) Applicant: Michael W Farrow, Warwick, MD (US)

(72) Inventor: Michael W Farrow, Warwick, MD (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/115,250

(22) Filed: Dec. 8, 2020

(51) Int. Cl.
*A01H 5/00* (2018.01)
*A01H 7/00* (2006.01)

(52) U.S. Cl.
USPC ..... Plt./214
CPC ..... *A01H 7/00* (2013.01)

(58) Field of Classification Search
USPC ..... Plt./214
CPC ..... A01H 7/00; A01H 5/12; A01H 5/00
See application file for complete search history.

*Primary Examiner* — Kent L Bell
(74) *Attorney, Agent, or Firm* — Cassandra Bright

(57) ABSTRACT

A new and distinct variety of *Juniperus* plant named 'FARROWJVBF' is disclosed, characterized by blue foliage and abundant blue fruits. Plants are dense with a pyramidal habit. The new cultivar is a *Juniperus*, suitable for ornamental garden purposes.

2 Drawing Sheets

Latin name of the genus and species: *Juniperus virginiana.*

Variety denomination: 'FARROWJVBF'.

BACKGROUND OF THE INVENTION

The new cultivar is a product of an open-pollination breeding program by the inventor, Michael W. Farrow. The open pollination resulting in 'FARROWJVBF' was made during 2009 at a commercial nursery in Warwick, Md. Selection of the new variety was made during 2010 at the same nursery. The seed parent of 'FARROWJVBF' is an unnamed, unpatented *Juniperus virginiana*. The pollen parent is unidentified.

After identifying the new variety as a potentially interesting selection, first propagation of 'FARROWJVBF' occurred by softwood cuttings at a commercial nursery in Warwick, Md. in 2010. The inventor continued controlled testing and propagation, assessing stability of the unique characteristics of this variety. Five generations have been reproduced and have shown that the unique features of this cultivar are stable and reproduced true to type.

SUMMARY OF THE INVENTION

The cultivar 'FARROWJVBF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWJVBF' These characteristics in combination distinguish 'FARROWJVBF' as a new and distinct *Juniperus* cultivar:

1. Blue foliage.
2. Dense plant with a pyramidal shape.
3. Abundant small blue fruit.

COMMERCIAL COMPARISON

'FARROWJVBF' can be compared to the known commercial variety *Juniperus virginiana* 'Burkii', unpatented. The varieties are similar in most horticultural characteristics, however, plants of 'FARROWJVBF' differ in the following ways:

1. New cultivar produces blue foliage, foliage of this comparator is more silver/gray.
2. Plants of the new variety are narrower than plants of this comparator.
3. Fruit of the new variety is blue; fruit of this comparator is gray.

PARENTAL COMPARISON

'FARROWJVBF' is similar to the seed parent in most horticultural characteristics, however, plants of 'FARROWJVBF' differ in the following:

1. The new cultivar has blue foliage; the seed parent has green foliage.
2. The new variety produces blue fruit; the seed parent produces green to blue fruit.

BRIEF DESCRIPTION OF THE PHOTOGRAPHS

Figure 1:
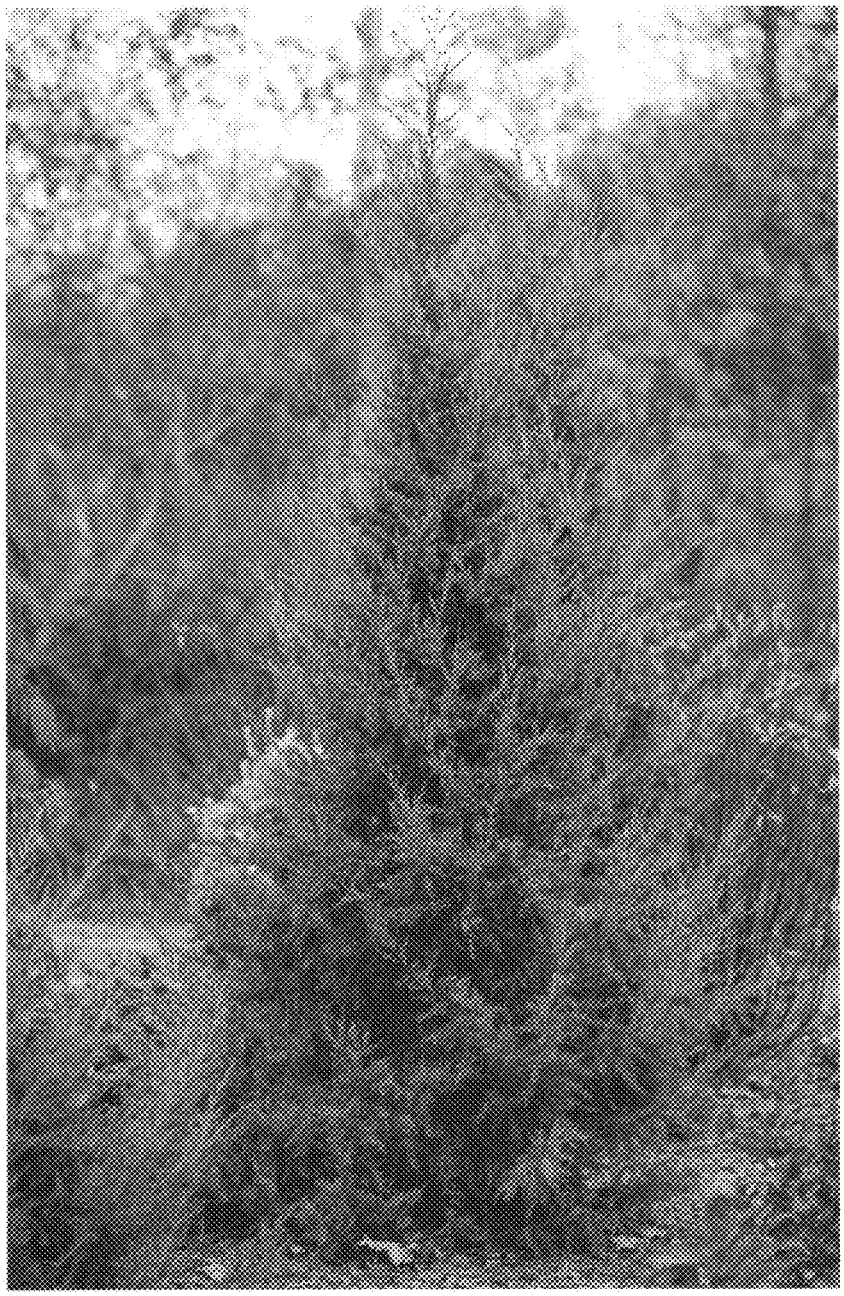

The accompanying photograph in FIG. 1 illustrates in full color a typical plant of 'FARROWJVBF' grown outdoors in Grand Haven, Mich. The plant in FIG. 1 is approximately 5 years old, and exhibit the characteristic dense and pyramidal growth.

Figure 2:
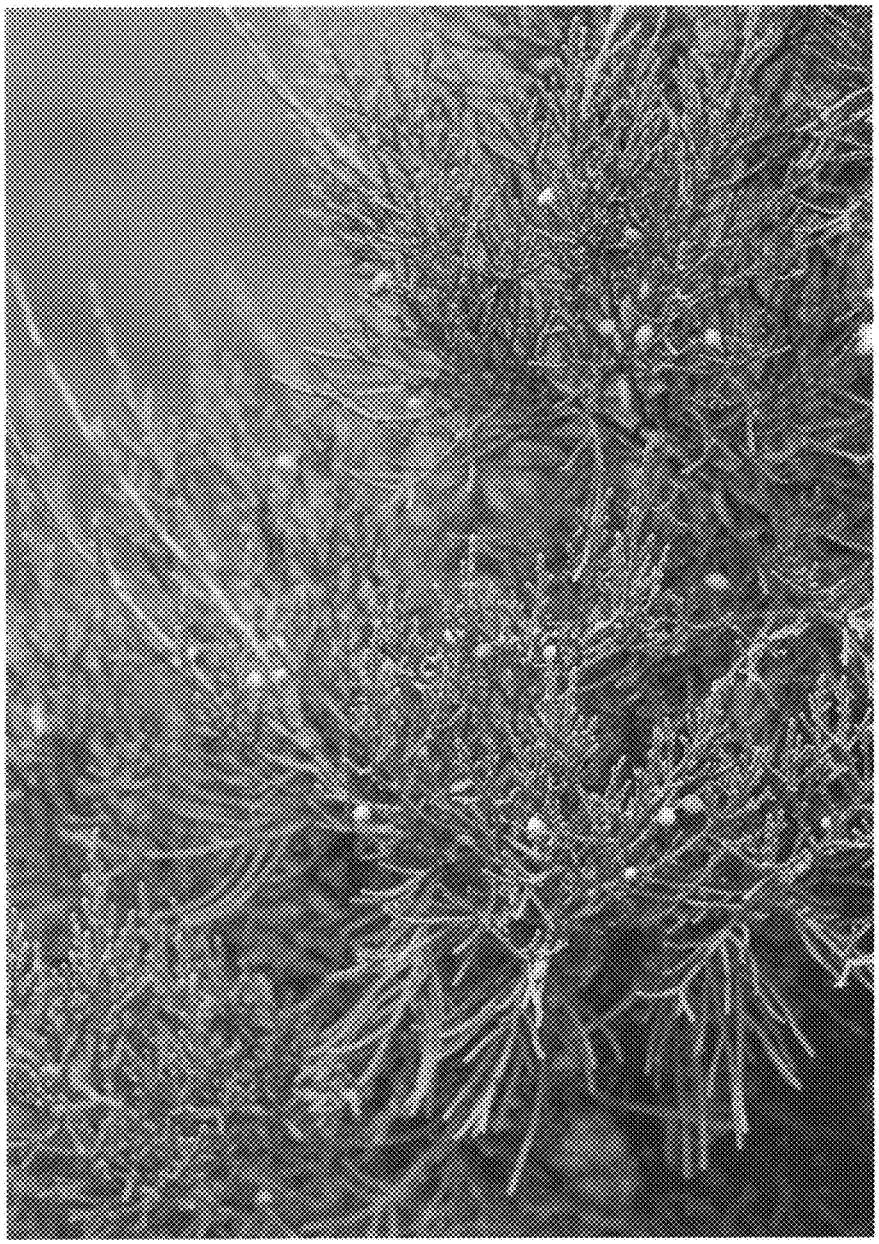

FIG. 2 illustrates a close-up view of the foliage and fruits.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWJVBF' plants grown in a poly greenhouse during Summer, in Grand Haven, Mich. The growing temperature ranged from 18° C. to 27° C. during the day and from 5° C. to 10° C. during the night. General light conditions are natural sunlight. Measurements and numerical values represent averages of typical plant types.

Botanical classification: *Juniperus virginiana* 'FARROWJVBF'.

PROPAGATION

Typical method: Softwood cuttings.
Time to initiate rooting: 120 days at approximately 10° C.
Time to produce a rooted young plant: 180 days at approximately 10° C. to 13° C.
Root description: Fine and fleshy roots present. Moderately well branched. Colored light brown, not accurately measured with an R.H.S. chart.

PLANT

Age of plant described: 1 to 2 years.
Container size of plant described: 1 gallon.
Growth habit: Evergreen tree. Upright, pyramidal.
Height: 44 cm.
Plant spread: 46 cm.
Typical growth rate: Slow.
Branching characteristics: Upright and outwards.
Angle: 45 to 90°.
Quantity of lateral branches: 10.
Length of lateral branches: 46 cm.
Diameter of lateral branches: 2 mm.
Lateral branch shape: Round.
Stem strength: Strong.
Stem color: Greyed-Orange 177D.
Internode length: Average 2 cm.
Thorns: About 5 mm long, colored near Greyed-Orange 177D. Dense.

FOLIAGE

Leaf:
*Arrangement*.—Alternate whorled scales.
*Shape of blade*.—Scale-like, developing into needles.
*Length*.—3 to 6 mm.
*Width*.—0.7 mm.
*Apex*.—Acute.
*Base*.—Truncated, fused.
*Margin*.—Entire.
*Texture of top surface*.—Smooth.
*Texture of bottom surface*.—Smooth.
*Foliage color*.—Young upperside: Near RHS Green 133B. Young underside: Near RHS Green 133B. Mature upperside: Near RHS Green 133B with overlay blue-Green 122C. Mature uneerside: Near RHS Green 133B with overlay blue-Green 122C.
*Venation*.—Not observable.
*Fragrance*.—Not observed.

FLOWER

Winter/spring bloom of inconspicuous dioecious flowers.

OTHER CHARACTERISTICS

Fruits: Berry-like cone. About 7 mm in diameter, colored near Blue 108D. Typically Fall through Winter.
Disease and pest resistance: Neither resistance nor susceptibility observed.
Drought tolerance: No tolerance for drought.
Temperature tolerance: Tolerates USDA Zones 4 through 9.

What is claimed is:

1. A new and distinct cultivar of *Juniperus* plant named 'FARROWJVBF' as herein illustrated and described.

* * * * *